(12) United States Patent
Dershem et al.

(10) Patent No.: US 6,211,320 B1
(45) Date of Patent: Apr. 3, 2001

(54) LOW VISCOSITY ACRYLATE MONOMERS FORMULATIONS CONTAINING SAME AND USES THEREFOR

(75) Inventors: Stephen M. Dershem; Jose A. Osuna, both of San Diego, CA (US)

(73) Assignee: Dexter Corporation, Windsor Locks, CT (US)

( * ) Notice: Subject to any disclaimer, the term of this patent is extended or adjusted under 35 U.S.C. 154(b) by 0 days.

(21) Appl. No.: 09/362,809

(22) Filed: Jul. 28, 1999

(51) Int. Cl.[7] ............................ C08F 220/12; C08L 55/00
(52) U.S. Cl. ..................... 526/329.1; 525/55; 525/242; 525/326.5; 525/329.7; 525/330.3; 526/317.1; 526/318; 526/318.1; 526/318.25; 524/553; 524/554
(58) Field of Search .................... 525/55, 242, 326.5, 525/329.7, 330.3; 526/317.1, 318, 318.1, 318.25, 329.1; 524/553, 554

(56) References Cited

U.S. PATENT DOCUMENTS 4,777,209 * 10/1988 Hefner, Jr. ........................ 525/28
5,621,019    4/1997  Nakano et al. .

FOREIGN PATENT DOCUMENTS

| 197 25 348 | 2/1998 | (DE) . |
| 0 141 610 | 5/1985 | (EP) . |
| 1 425 588 | 12/1965 | (FR) . |
| 984 827 | 3/1965 | (GB) . |

OTHER PUBLICATIONS

Takeshi et al., "Alicyclic acrylate polymers for optical materials," *Chemical Abstracts* 111(14) (Oct. 2, 1989) (abstract No. 115941k, XP000250354).3

* cited by examiner

*Primary Examiner*—Samuel A. Acquah
(74) *Attorney, Agent, or Firm*—Gray Cary Ware & Freidenrich LLP; Stephen E. Reiter

(57) ABSTRACT

In accordance with the present invention, there are provided low viscosity acrylate monomers, and compositions based on same having low moisture resistance (and, hence are much less prone to give rise to "popcorning"), excellent handling properties (i.e., generally existing as a fluid material which does not require the addition of solvent to facilitate the use thereof), and excellent performance properties (e.g., good dielectric properties).

14 Claims, No Drawings

LOW VISCOSITY ACRYLATE MONOMERS FORMULATIONS CONTAINING SAME AND USES THEREFOR

FIELD OF THE INVENTION

The present invention relates to novel acrylate monomers. Invention monomers are noteworthy for their low viscosity and reactivity and are useful in a variety of applications related to the preparation of components employed in the electronics industry. In another embodiment of the invention, there are provided methods for preparing low viscosity acrylate monomers. In a particular aspect, the present invention relates to formulations useful for the preparation of laminates. In another aspect, the present invention relates to formulations useful for the preparation of solder masks. In yet another aspect, the present invention relates to formulations useful for the preparation of liquid encapsulant for electronic components. In still another aspect, the present invention relates to formulations useful for the preparation of non-hermetic electronic packages. In a still further aspect, the present invention relates to formulations useful for the preparation of die attach compositions.

BACKGROUND OF THE INVENTION

As the electronics industry advances, and production of light weight components increases, the development of new materials gives producers increased options for further improving the performance and ease of manufacture of such components. Materials used in the manufacture of electronic components include the resin required for the preparation of prepregs (which are, in turn, used for the preparation of multilayered printed circuit boards and printed wiring boards), resins used for the preparation of solder masks (which define solder areas on the multilayered printed wiring board), and resins used for preparation of glob top (which protects microelectronic devices from the environment).

Multilayered printed circuit boards are currently produced mainly by (a) a mass laminating technique and (b) a pin laminating technique. In these techniques, a printed circuit board for inner layer use (hereinafter, referred to as "inner-layer board") is first manufactured. This inner-layer board is combined with prepregs and then a copper foil or a single-side copper-clad laminate and the superposed laminating materials are laminated to give a multilayered board, both sides of which are constituted by a copper foil. This multi-layered structure is subjected to processing steps such as steps for forming through-holes, outer-layer printed circuits, etc.

The initial manufacture of resins used in laminates is usually conducted by chemical producers and supplied to the trade in a workable form. Addition of a curing agent or catalyst, as well as optional components such as diluents, flow promoters, fire retardants, and other modifying resins is performed by the user. This may be done in the interest of customization to the application or to ensure that pre-reaction of the formulation does not occur.

The catalyzed resin system is placed into a dip tank in which the glass cloth is immersed. The wet-coated cloth is squeezed between metering rolls to leave a measured amount of the resin system. Then it passes into a tunnel drier to remove any volatile materials (e.g., solvent if present) and usually to react the resin to a predetermined molecular weight. This ensures the proper amount of flow during lamination.

After the coated cloth has passed through the tunnel drier, the resin is high enough in $T_g$ to permit handling. At this stage, it is called prepreg; it can be cut into sheets or stored in roll form. Storage is often at room temperature, although some formulations require refrigeration.

Cut to size, sheets of prepreg are stacked between polished steel plates for placement in a laminating press. If printed circuits are to be made from the cured stock, copper foil is placed at the two surfaces of the stack. Otherwise, separator sheets or lubricants ensure removal of the plates from the cured laminate.

The conditions under which cure takes place vary with the resin type, thickness of the laminate, and other factors. Resin cure might be carried out, for example, at 175° C., from 250 to 1,000 psi, and for 30 to 60 minutes at temperature, followed by cooling. Certain resins (e.g., heat-resistant polymers) may require 200° C. or more for complete cure. Since steam-heated presses do not operate well above 175° C., frequently a partial cure is effected at this temperature and the remainder carried out in an oven at the higher temperature. Warpage is a definite possibility under such a procedure. Control of dimensional stability of laminate material and stability of assembled boards are both becoming more important. Towards that end, the trend is toward use of higher $T_g$ resin material, laminated in a vacuum process to meet the fabrication-tolerance requirements and to reduce moisture absorption.

The behavior of high-reliability printed-circuit laminates may be improved by the addition of silane couplers to the resin materials employed for preparation of laminate. While the addition of couplers is intended to permit the resulting composites to be used in uncontrolled environments, many prior art materials appear to fail under certain conditions of high humidity and voltage stress. The result is the creation of copper-shorting filament plated along the glass surface. These may penetrate from one circuit element to another. Because the accelerating factors for this phenomenon are ionic contamination, humidity, voltage, and temperature, the chief test for suitability of the selected resin material and coupler for the intended use is the electrical resistance between interconnection lines or holes under voltage stress at high humidity.

When performing as intended, the coupler serves to bond the glass and cured resin strongly so that they act as a composite, although with anisotropic mechanical properties. Residual stresses in this composite affect the dimensional stability thereof. One source of these stresses is the glass fabric itself. The warp (machine direction) strands are flattened by tension during the impregnation process, while the crimp of the fill fibers is actually increased. Both are flattened during lamination. Repeat pressing raises the cured resin above its $T_g$; the softened material allows the glass fibers to relax, changing dimension. Temperature variation across the surface of the laminate during cure, resin flow to fill around elements in already circuitized substrates, as well as hole drilling; all create stress-induced dimensional change. Cross orienting alternate plies of the glass cloth can compensate glass-cloth tension, but in most cases, tracking such factors is not straightforward.

As a consequence, detailed correlation is lacking between dimensional change and the factors most predictive models assume for deformation; orthotopic contraction, warp, twist, and other high-order strain functions. Nonetheless, general effects are discernible, and the complex sequence of processes used to make multilayer boards is monitored and controlled based on computer predictive models derived from highly precise measurement techniques. This assures that the element in each layer will register to the others in the composite. Because moisture and temperature affect dimensions significantly compared with the factors discussed, prepregs, cores, and subcomposites are often temperature and humidity stabilized at critical process steps.

Another common use of resins in the electronics industry is for the preparation of solder masks. Solder mask is used to prevent excessive flow of solder in plastic packages. The material used must maintain the integrity of the physical, chemical, mechanical and environmentally related properties of the package. Solder masks were originally intended to be used on printed wiring boards (PWBs) as an aid to manufacturing, reducing the need for touch-up after machine soldering, reducing solder consumption, and providing mechanical protection for the main portion of the circuitry.

The main type of solder mask employed in the art is the "liquid photoimageable" solder mask. There are three primary methods of applying this type of solder mask: flood screen-coating, curtain and spray coating. Each method has both advantages and drawbacks. Screen coating, for example, is efficient in material usage, but through-holes may be plugged in the process. These holes must then be cleared during development. Curtain coating is also efficient, but it is also a much slower process due to the fact that only one side of a board can be coated at a time. Spray coating is the best method to accomplish complete fill and trace application, but this technique can result in substantial material losses (e.g., in the range of 10–30% waste).

Another common use of resins in the electronics industry is as a liquid encapsulant (also referred to as "glob top"), wherein an aliquot of resin material is used to encase a component to protect it from certain stresses and from exposure to the environment. To meet the industry's ever-increasing demand for device reliability, materials for encapsulant applications must meet increasingly stringent property requirements. Such requirements include excellent moisture resistance, ionic purity, low dielectric constant and good thermal properties. In the absence of these properties, especially in the presence of moisture and ionic impurities, corrosion (and ultimately failure of the device) will likely occur.

Yet another common use of resins in the electronics industry is in the preparation of non-hermetic electronic packages. Examples of such packages are ball grid array (BGA) assemblies, super ball grid arrays, IC memory cards, chip carriers, hybrid circuits, chip-on-board, multi-chip modules, pin grid arrays, and the like. In these structures, moisture resistance is an important consideration, both in terms of handling during assembly and reliability of the finished part. For example, absorption of moisture during assembly frequently leads to "popcorning" (the sometimes violent release of absorbed moisture upon heating to solder reflow temperatures). Accordingly, the development of moisture resistant resins for use in the preparation of non-hermetic electronic packages would be of great benefit to the art.

Accordingly, what is still needed in the art are materials which have good workability properties (e.g., fluid under typical processing conditions) and good performance properties (e.g., good adhesion, moisture resistance, etc.).

BRIEF DESCRIPTION OF THE INVENTION

In accordance with the present invention, there are provided low viscosity acrylate monomers that are useful for the preparation of compositions having excellent moisture resistance (and, hence are much less prone to give rise to "popcorning"), excellent handling properties (i.e., generally existing as a fluid material which does not require the addition of solvent to facilitate the use thereof), and excellent performance properties (e.g., good dielectric properties). Compositions and formulations employing invention monomers demonstrate excellent adhesion to copper substrates, and also have superior electrical conductivity. Compositions containing invention monomers are useful in a variety of applications. For example, in one embodiment of the present invention, there are provided thermosetting resins. Depending on the formulation, invention resins are useful for the preparation of laminates, as solder masks, as liquid encapsulant for electronic components, as die attach compositions, and the like.

DETAILED DESCRIPTION OF THE INVENTION

In accordance with the present invention, there are provided acrylate derivatives of oligomers of optionally substituted cyclopentadiene. It is presently contemplated that the oligomers of optionally substituted cyclopentadiene comprise one or more bicyloheptane moieties.

Various substituents may be incorporated into the bicyloheptane moieties without compromising the performance properties of invention compounds. Accordingly, in one embodiment of the present invention, one or more of the bicycloheptane moieties is optionally independently substituted up to 2 substituents independently selected from lower alkyls or halogens.

As those of skill in the art will understand, oligomers of cyclopentadiene will comprise different chemical structures depending on the mode of synthesis and degree of oligomerization. Accordingly, invention acrylates are derivatives of oligomers having one or more of the following structures:

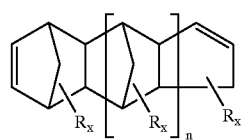

(I)

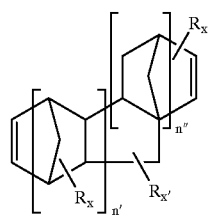

(II)

wherein:
each R is independently a lower alkyl or a halogen,
n is 1, 2, or 3,
the sum of n'+n" is 1, 2, or 3,
each x is independently 0, 1 or 2, and
x is 0, 1, 2.

As will be further understood by those of skill in the art, oligomers of cyclopentadiene may take the form of bicycloheptenyl moieties. Accordingly, in another embodiment of the present invention there are provided acrylate derivatives of optionally substituted bicycloheptenyl-containing polycyclic moieties having one or more of the following structures:

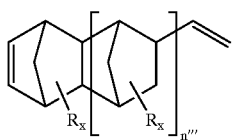

(III)

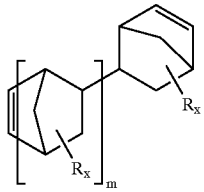

(IV)

wherein:
  each R is independently a lower alkyl or a halogen,
  n''' is 1, 2, 3, 4, or 5,
  m is 1, 2, 3, 4, or 5, and
  each x is independently 0, 1 or 2.

Invention acrylates may be mono- or bi-functional. Accordingly, in another aspect of the present invention, there are provided bifunctional acrylate monomers having one or more of the following structures:

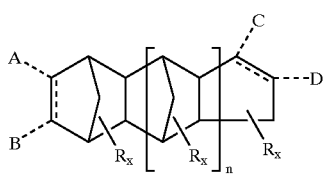

(V)

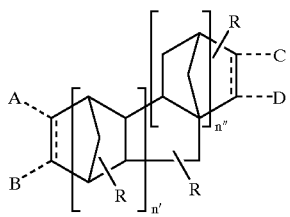

(VI)

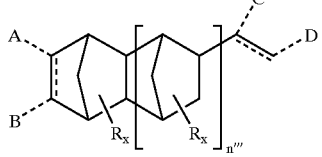

(VII)

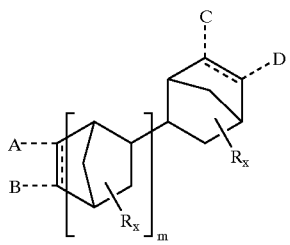

(VIII)

wherein:
  at least one of A and B, and/or one of C and D is a (meth)acrylate moiety, wherein any of A, B, C, and D that are not (meth)acrylate are H or a functional group,
  each R is independently a lower alkyl or a halogen,
  n is 1, 2 or 3,
  the sum of n'+n" is 1, 2, or 3,
  n''' is 1, 2, 3, 4, or 5,
  m is 1, 2, 3, 4, or 5,
  each x is independently 0, 1 or 2, and
  x' is 0, 1, 2.

Other functional groups which are usefully incorporated into invention mono or bifunctional monomers at the A, B, C, or D positions (in addition to the at least one acrylate functional group A, B, C or D, as defined above), are maleimido, norbornenyl, cyanate ester, anhydrides, carboxylic acids, epoxides, amides, sulfides, polyhydroxy hydrocarbyls, and the like.

As will be understood by those of skill in the art, the dashed lines employed in structures depicted herein signify bonds present in alternative aspects of the present invention. Thus, the dashed line inside a ring indicates an alternative structure having a double bond. The two dashed lines extending outside of a ring (to A and B, and/or C and D) signify alternative structures having additional functional substituents on the ring instead of a double bond at that position. Thus, for example, when an acrylate moiety is present, there is no ring double bond at that position, and the converse is also true.

Invention acrylates may be linked with other functional moieties, with or without a bridging group therebetween. Thus, in still another embodiment of the present invention, there are provided bifunctional monomers having the following structure:

X—Y—Z wherein:
  Y is an optional bridging group,
  X is an acrylate derivative of an oligomer of optionally substituted cyclopentadiene, or a radical having one of the following structures:

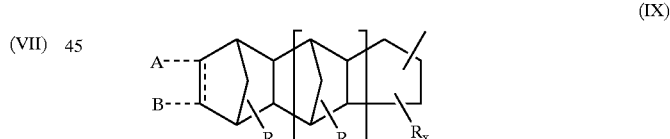

(IX)

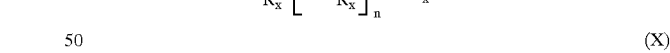

(X)

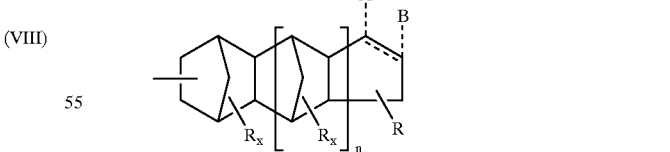

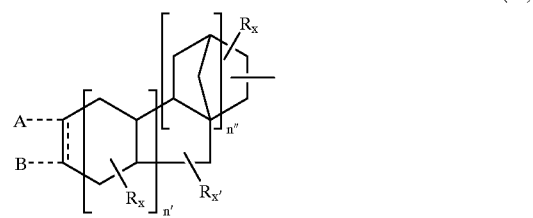

(XI)

-continued

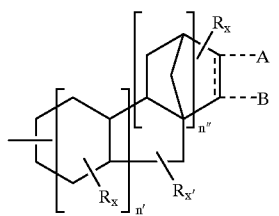
(XII)

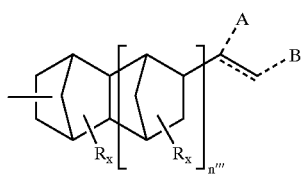
(XIII)

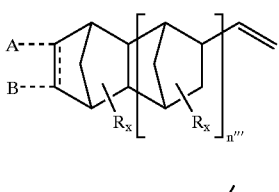
(XIV)

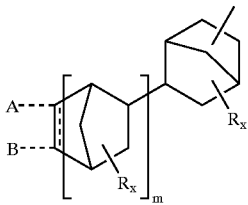
(XV)

wherein:
A or B is a (meth)acrylate moiety, wherein the non-(meth) acrylate member of the A/B pair is H,
each R is independently a lower alkyl or a halogen,
n is 1, 2 or 3,
the sum of n'+n" is 1, 2 or 3,
n''' is 1, 2, 3, 4, or 5,
m is 1, 2, 3, 4, or 5,
each x is independently 0, 1 or 2, and
x' is 0, 1, 2, and
Z is a trimer, tetramer or pentamer of optionally substituted cyclopentadiene bearing at least one functional group, a radical having one of said structures (IX), (X), (XI), (XII), (XIII), (XIV), or (XV), an epoxy, or a cycloaliphatic moiety bearing at least one functional group.

In one embodiment of the foregoing bifunctional monomer, Z is an oligomer of optionally substituted cyclopentadiene bearing at least one functional group, or a radical having one of said structures (IX), (X), (XI), (XII), (XIII), (XIV), or (XV).

Optional bridging groups Y contemplated for use in the practice of the present invention include siloxane, (oxy) alkylene, (oxy) arylene, and the like.

Siloxanes contemplated for use in the practice of the present invention have the structure:

$$-(CR''_2)_{m'}-[Si(R''')_2-O]_{q'}-Si(R''')_2-(CR''_2)_{m''}-$$

wherein:
each R" is independently hydrogen, a lower alkyl or aryl,
each R''' is independently selected from hydrogen, oxygen, lower (oxy) alkyl or (oxy) aryl,
m' falls in the range of 0 up to about 10,
m" falls in the range of 0 up to about 10, and
q' falls in the range of 1 up to 50.

(Oxy)alkylenes contemplated for use in the practice of the present invention have the structure:

$$-[(CR''_2)_{r}-(O-)_{q''}]_{q}-(CR''_2)_{s}-$$

wherein:
each R" is as defined above,
m' falls in the range of 1 up to about 10,
m''' falls in the range of 1 up to about 10,
q" is 0 or 1 and
q falls in the range of 1 up to 50.

As described above, other functional groups which are usefully incorporated into invention bifunctional monomers (in addition to the at least one (meth)acrylate functional group A and/or B, C and/or D as defined above), are maleimido, norbornenyl, cyanate ester, anhydrides, carboxylic acids, epoxides, amides, sulfides, polyhydroxy hydrocarbyls, and the like.

Low viscosity acrylate monomers described herein are particularly well suited for use in the synthesis of thermosetting resins having excellent handling properties, a high degree of hydrophobicity and low susceptibility to hydrolysis. Therefore, in accordance with another embodiment of the present invention, there are provided thermosetting resins comprising:
(a) cycloaliphatic bifunctional acrylate monomers having one or more of the structures VII through XII, wherein:
A, B, R, n, n'+n", n''', m, x and x' are defined as above,
(b) optionally, in the range of about 5 up to about 95 wt % of a monovinyl compound having the structure XVI as follows:

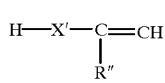
(XVI)

wherein $R^a$ is H or methyl and X' is a hydrophobic bridging group having in the range of about 7 up to about 400 carbon atoms, optionally linked by a suitable linking moiety (e.g., an ester, an ether, an amide, or the like);
(c) in the range of about 0.1 up to about 3 wt % of at least one curing agent (i.e., catalyst), based on the total weight of the composition;
(d) optionally, in the range of about 1.0 up to about 60 wt % of at least one polyunsaturated comonomer, based on the total weight of the composition; and
(e) optionally, a diluent.

Invention compositions are noteworthy for their excellent handling properties. Such compositions have desirably low viscosities which facilitate dispense operations. Typical viscosities fall in the range of about 10 up to about 12,000 centipoise, with viscosities in the range of about 70 up to about 2,000 centipoise being presently preferred.

The bridging groups, —X'—, contemplated by the above generic formula (i.e., structure XVI) include divalent or polyvalent radicals such as 4,8-bis(substituted)-tricyclo [5.2.1.0$^{2,6}$]decane, derivatives of dimer-diol (as available, for example, from Unichema North America, Chicago, Ill., under the designation Pripol 2033), i.e.,

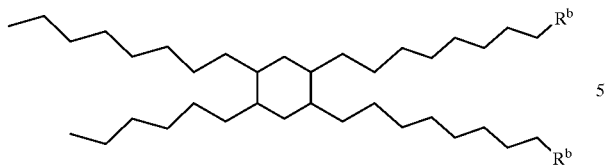

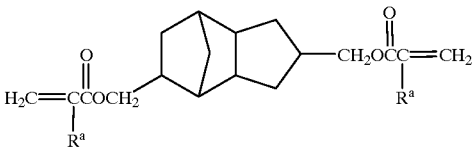

wherein $R^a$ is H or methyl;

wherein $R^b$ is an acrylate, methacrylate, vinyl ether, vinyl ester, allyl ether, allyl ester, and the like; derivatives of perhydro bisphenol A as well as other bisphenol derivatives, biphenyl derivatives, triphenyl methyl derivatives, 1,2-polybutadiene derivatives, 1,4-polybutadiene derivatives, mixed 1,2- and 1,4-polybutadiene derivatives, hydrogenated polybutadiene derivatives, polybutene derivatives, and the like.

the diacrylate ester of dimer-diol (as available, for example, from Unichema North America, Chicago, Ill., under the designation Pripol 2033), i.e.,

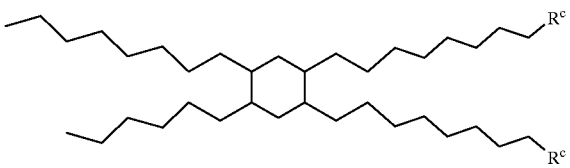

Polyvinyl compounds contemplated for use as component (d) in accordance with the present invention include acrylates of structure XVII as follows:

when $R^c$=$H_2C$=CH—C(O)O—;

the diacrylate of 10,11-dioctyl-1,20-eicosane, the diacrylate of perhydro bisphenol A, i.e.,

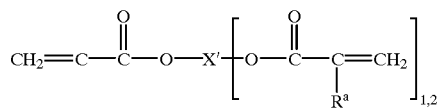
(XVII)

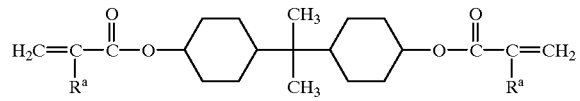

wherein X' is a hydrophobic cyclic or acyclic aliphatic or aromatic bridging group having in the range of about 7 up to about 40 carbon atoms, and $R^a$ is H or methyl.

wherein $R^a$ is H or methyl;

Acrylates embraced by the above generic formula include 4,8-bis(acryloxymethyl)-tricyclo[$5.2.1.0^{2,6}$]decane, i.e., as well as the bisphenol derivatives:

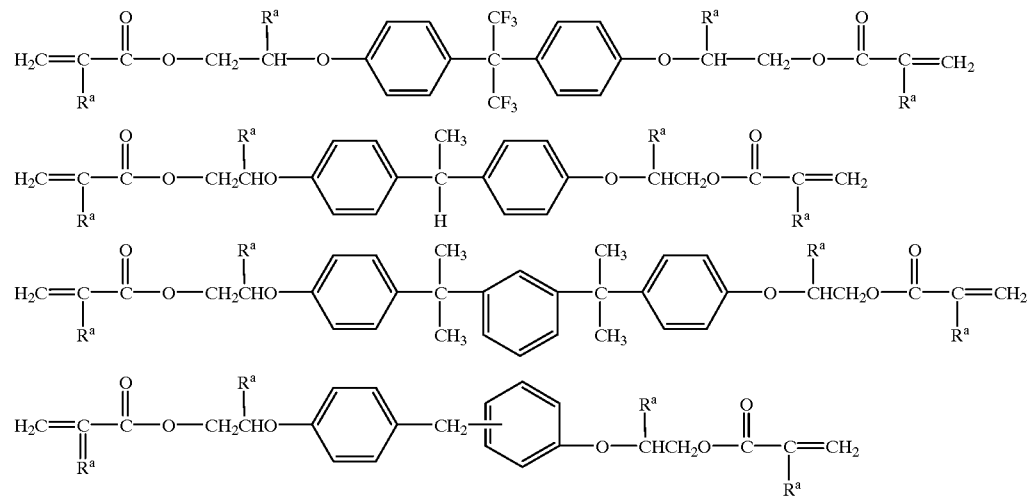

wherein $R^a$ is H or methyl;

the biphenyl derivatives:

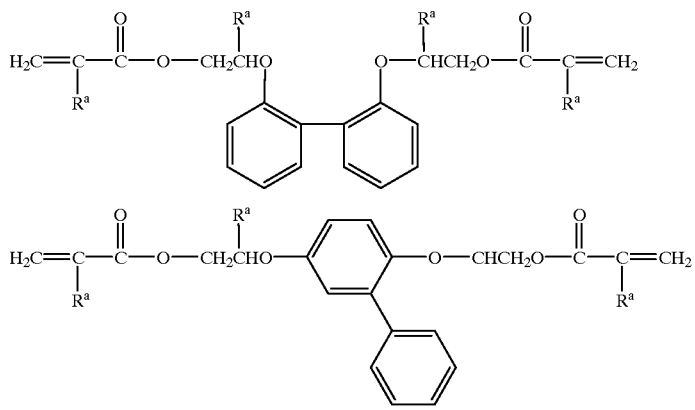

wherein $R^a$ is H or methyl;
the triphenyl methyl derivative:

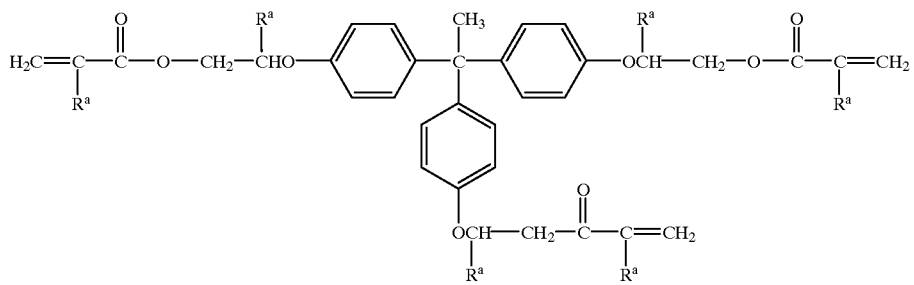

wherein $R^a$ is H or methyl;
and the like.

Other polyvinyl compounds contemplated for use as component (d) with invention thermosetting resins include bis (para-substituted styrene) derivatives of structure XVIII as follows:

(XVIII)

$$CH_2=\underset{R^a}{C}-Ar-X'-\left[Ar-\underset{R^a}{C}=CH_2\right]_{1,2}$$

wherein X' is a hydrophobic cyclic or acyclic aliphatic bridging group having in the range of about 7 up to about 40 carbon atoms, and R" is H or methyl.

Styrenic compounds embraced by the above generic formula include 4,8-bis(paravinylphenol)-tricyclo[5.2.1.0$^{2,6}$] decane:

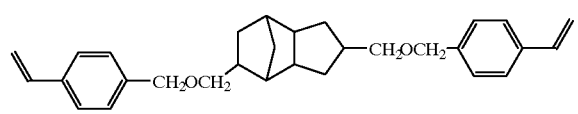

and the homolog thereof having the structure:

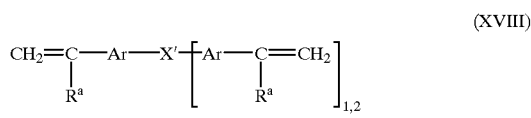

as well as styrenic derivatives of the various bisphenol backbones, biphenyl backbones and triphenyl methane backbones set forth above, and the like.

Additional polyvinyl compounds contemplated for use as component (d) with invention thermosetting resins also include polyvinyl ethers of structure XIX as follows:

(XIX)

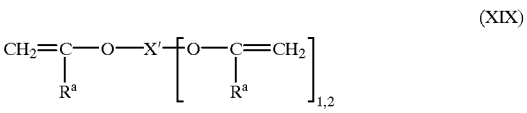

wherein X' is a hydrophobic cyclic or acyclic aliphatic bridging group having in the range of about 7 up to about 40 carbon atoms, and $R^a$ is H or methyl.

Vinyl ethers embraced by the above generic formula include 4,8-bis(paravinyl hydroxymethyl benzene)-tricyclo [5.2.1.0$^{2,6}$]decane, the divinyl ether having the structure:

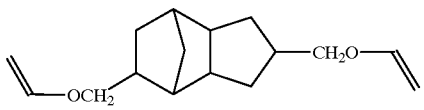

as well as vinyl ether derivatives of the various bisphenol backbones, biphenyl backbones and triphenyl methane backbones set forth above, and the like.

Still further polyvinyl compounds contemplated for use as component (d) in accordance with invention thermosetting resins also include polyvinyl esters of structure XX as follows:

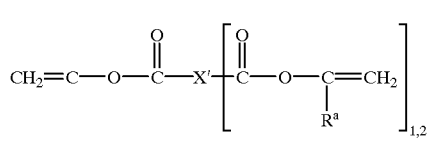

(XX)

wherein X' is a hydrophobic cyclic or acyclic aliphatic bridging group having in the range of about 7 up to about 40 carbon atoms, and $R^a$ is H or methyl.

Polyvinyl esters embraced by the above generic formula XX include the 4,8-divinyl ester of tricyclo[5.2.1.0$^{2,6}$] decane, i.e.,

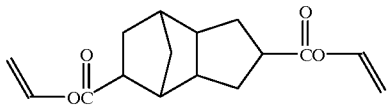

the divinyl ester of dimer diacid, i.e.,

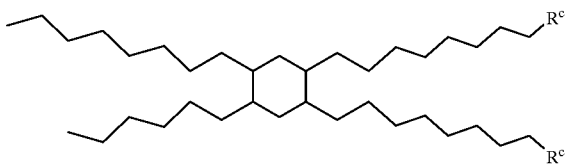

when $R^c$=H$_2$C=CH—O—C(O)—, cyclohexyl derivatives such as:

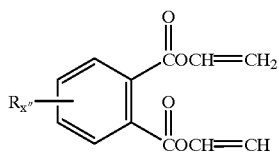

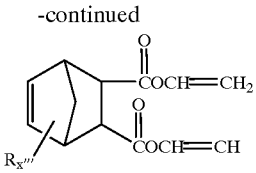

wherein R is as defined above, and x''' is 0 up to 3; as well as vinyl ester derivatives of the various bisphenol backbones, biphenyl backbones and triphenyl methane backbones set forth above, and the like.

Still further polyvinyl compounds contemplated for use as component (d) in invention resins polyvinyl amides of structure XXI as follows:

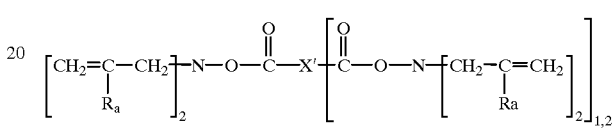

(XXI)

wherein X' is a hydrophobic cyclic or acyclic aliphatic bridging group having in the range of about 7 up to about 40 carbon atoms, and $R^a$ is H or methyl.

Bisallyl amides embraced by the above generic formula XXI include polyvinyl amides having the structure:

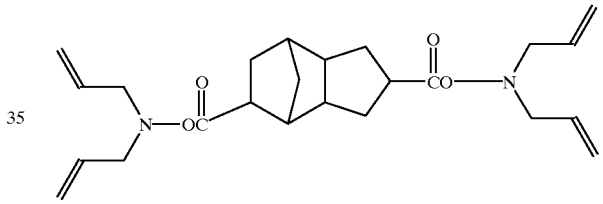

as well as bisallyl amide derivatives of the various bisphenol backbones, biphenyl backbones and triphenyl methane backbones set forth above, and the like.

Other polyunsaturated comonomers contemplated for use as component (d) in invention resins include polybutadiene, hydrogenated polybutadiene (including partially hydrogenated polybutadiene), maleinized polybutadiene, acrylonitrile copolymers, polyterpenes, and the like.

Those of skill in the art recognize that a variety of monofunctional counterparts (component (b) of invention resins) of the above-described polyvinyl compounds are commercially available and/or can readily be prepared, such as, for example, the monofunctional compounds:

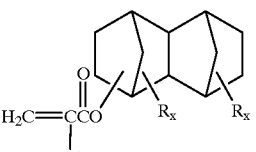

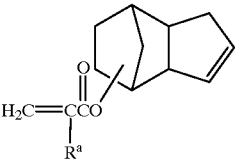

-continued

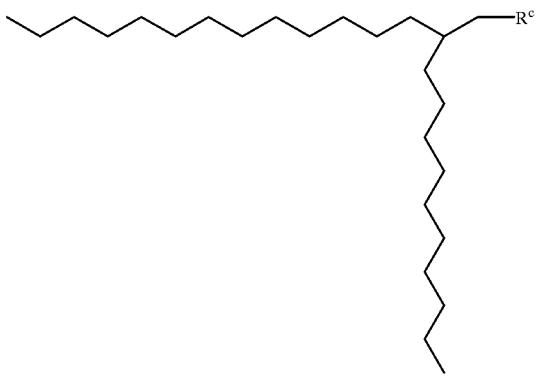

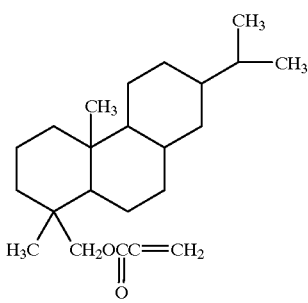

wherein R, $R^a$, $R^c$, x, and x' are as defined hereinabove.

It is also possible for compounds bearing a plurality of vinyl functionalities to be employed in the practice of the present invention, such as, for example, the polyfunctional compound set forth below

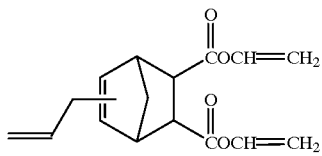

As readily recognized by those of skill in the art, a wide variety of curing catalysts can be employed in the preparation of invention resins. The preferred catalyst to be used will, of course, depend on the monomer employed. Monomers contemplated for use herein cure by a free radical mechanism, thus free radical initiators such as peroxy esters, peroxy carbonates, hydroperoxides, alkylperoxides, arylperoxides, azo compounds, benzopinacole, Barton esters, and the like can be employed.

In addition, catalysts which promote cationic cure can also be used. Such catalysts are especially useful when the monomers used are polyvinyl ethers. Examples of suitable cationic cure catalysts include onium salts, iodonium salts, sulfonium salts, and the like.

Diluents contemplated for optional inclusion as component (e) in invention resins include any non-reactive or reactive diluent. Reactive diluents which may be employed include those which, in combination with the vinyl monomer-based formulations described herein, form a thermosetting resin composition. Such reactive diluents include acrylates and methacrylates of monofunctional and polyfunctional alcohols, ethylenically unsaturated compounds, styrenic monomers (i.e., ethers derived from the reaction of vinyl benzyl chlorides with mono-, di-, or trifunctional hydroxy compounds), and the like. When used, reactive diluents are typically present in the range of about 5 up to 15 wt %, relative to the weight of the base formulation.

While the use of inert diluents is not excluded from the practice of the present invention, it is generally preferred that compositions according to the invention remain substantially free of solvent, so as to avoid the potentially detrimental effects thereof, e.g., creation of voids caused by solvent escape, the environmental impact of vaporized solvent, the redeposition of outgassed molecules on the surface of the article, and the like. When used, suitable inert diluents include dimethylformamide, dimethylacetamide, N-methylpyrrolidone, toluene, xylene, methylene chloride, tetrahydrofuran, glycol ethers, methyl ethyl ketone or monoalkyl or dialkyl ethers of ethylene glycol, polyethylene glycol, propylene glycol, polypropylene glycol, and the like. When used, inert diluents are typically present in the range of about 10 up to 40 wt %, relative to the weight of the base formulation.

Invention thermosetting resins are useful for a variety of applications, e.g., die-attach pastes. Thermosetting resin compositions employed for the preparation of die-attach pastes according to the invention further comprise:

(f) a filler, and (g) optionally, up to 10 wt % of at least one coupling agent, based on the total weight of the composition.

Coupling agents contemplated for use herein include silicate esters, metal acrylate salts, titanates, compounds containing a co-polymerizable group and a chelating ligand, and the like.

Fillers contemplated for use as component (f) in invention resins may optionally be conductive (electrically and/or thermally). Electrically conductive fillers contemplated for use in the practice of the present invention include, for example, silver, nickel, gold, cobalt, copper, aluminum, graphite, silver-coated graphite, nickel-coated graphite fillers, alloys of such metals, and mixtures thereof, and the like. Both powder and flake forms of filler may be used in the attach paste compositions of the present invention. Preferably, the flake has a thickness of less than about 2 microns, with planar dimensions of about 20 to about 25 microns. Flake employed herein preferably has a surface area of about 0.15 to 5.0 $m^2/g$ and a tap density of about 0.4 up to about 5.5 g/cc. It is presently preferred that powder employed in the practice of the present invention has a diameter of about 0.5 to 15 microns.

Thermally conductive fillers contemplated for use in the practice of the present invention include, for example, aluminum nitride, boron nitride, silicon carbide, diamond, graphite, beryllium oxide, magnesia, silica, alumina, and the like. Preferably, the particle size of these fillers will be about 20 μm. If aluminum nitride is used as a filler, it is preferred that it be passivated via an adherent, conformal coating (e.g., silica, or the like).

Electrically and/or thermally conductive fillers are optionally (and preferably) rendered substantially free of catalytically active metal ions by treatment with chelating agents, reducing agents, nonionic lubricating agents, or mixtures of such agents. Such treatment is described in U.S. Pat. No. 5,447,988, which is incorporated by reference herein in its entirety.

Optionally, a filler may be used that is neither an electrical nor thermal conductor. Such fillers may be desirable to impart some other property such as a reduced dielectric constant, improved toughness, increased hydrophobicity, and the like. Examples of such fillers include perfluorinated hydrocarbon polymers (i.e., TEFLON™), thermoplastic polymers, thermoplastic elastomers, mica, fused silica, and the like.

In other aspects, invention resin compositions can optionally further contain one or more of the following additional components: anti-oxidants/inhibitors, bleed control agents, adhesion promoters, flexibilizers, dyes, pigments, and the like.

Anti-oxidants/inhibitors contemplated for use in the practice of the present invention include hindered phenols (e.g., BHT (butylated hydroxytoluene), BHA (butylated hydroxyanisole), TBHQ (tertiary-butyl hydroquinone), 2,2'-methylenebis(6-tertiarybutyl-p-cresol), and the like), hindered amines (e.g., diphenylamine, N,N'-bis(1,4-dimethylpentyl-p-phenylene diamine, N-(4-anilinophenyl) methacrylamide, 4,4'-bis(,dimethylbenzyl) diphenylamine, and the like), phosphites, hindered amine N-oxides (e.g., 2,2,6,6-tetramethyl-1-piperidinyloxy, free radical (TEMPO)), quinones (e.g., benzoquinone, naphthoquinone, 2,5-dichlorobenzoquinone, and the like), and the like. When used, the quantity of anti-oxidant typically falls in the range of about 100 up to 2000 ppm, relative to the weight of the base formulation.

Anti-bleed agents contemplated for use in the practice of the present invention include cationic surfactants, tertiary amines, tertiary phosphines, amphoteric surfactants, polyfunctional compounds, and the like, as well as mixtures of any two or more thereof. Those of skill in the art recognize that the quantity of bleed control agent employed in the practice of the present invention can vary widely, typically falling in the range of about 0.1 up to about 10 wt %, relative to the weight of the base formulation.

Adhesion promoters contemplated for use in the practice of the present invention include polymers that have pendant acid or latent acid groups that can increase adhesion. An example is the Ricon R-130 20% maleated (Ricon Resins, Inc., Grand Junction, Colo.), a polybutadiene with anhydride groups that can react with a surface to increase adhesion. When present, adhesion promoters are typically present in the range of about 5 up to 30 wt %, relative to the weight of the base formulation.

Flexibilizers contemplated for use in the practice of the present invention include branched polyalkanes or polysiloxanes that lower the $T_g$ of the formulation. An example of such a material would be polybutadienes such as the Ricon R-130 as described hereinabove. When present, flexibilizers are typically present in the range of about 15 up to about 60 wt %, relative to the weight of the base formulation.

Dyes contemplated for use in the practice of the present invention include nigrosine, Orasol blue GN, phthalocyanines, and the like. When used, organic dyes in relatively low amounts (i.e., amounts less than about 0.2 wt %) provide contrast.

Pigments contemplated for use in the practice of the present invention include any particulate material added solely for the purpose of imparting color to the formulation, e.g., carbon black, metal oxides (e.g., $Fe_2O_3$, titanium oxide), and the like. When present, pigments are typically present in the range of about 0.5 up to about 5 wt %, relative to the weight of the base formulation.

As readily recognized by those of skill in the art, the quantity of the various components employed to prepare invention compositions can vary within wide ranges. For example, preferred die-attach compositions contemplated for use in accordance with the present invention comprise:

in the range of about 10 up to about 50 wt % of a thermosetting resin composition (with in the range of about 15–35 wt % being especially preferred), and in the range of about 50 up to about 90 wt % of a conductive filler (with in the range of about 65–85 wt % being especially preferred).

Preferred thermosetting resin compositions contemplated for use in accordance with the present invention comprise:

in the range of about 5 up to about 90 wt % of said combination of invention bifunctional monomers, in the range of about 5 up to about 75 wt % of said monovinyl compound having the structure XVI, in the range of about 0.5 up to about 2 wt % of said at least one free radical initiator, in the range of about 5 up to about 45 wt % of said at least one polyunsaturated comonomer, and in the range of about 0.1 up to about 5 wt % of said coupling agent.

In accordance with another embodiment of the present invention, there are provided assemblies comprising a microelectronic device permanently adhered to a substrate by a cured aliquot of the die attach paste according to the invention, as described in detail herein. Examples of the types of articles contemplated for preparation in accordance with the present invention include laminated circuit boards (i.e., the first article and the second article are separate layers of a laminate structure), printed wiring boards, and the like.

Examples of the base materials contemplated for use in the preparation of laminates include woven fabrics of various glasses such as E-glass, S-glass, SII-glass, D-glass, quartz glass, and the like, and other inorganic woven fabrics such as alumina paper; woven fabrics made of super heat-resistant resins such as all-aromatic polyamides, polyimides, fluoroplastics, poly(phenylene sulfide), polyetheretherketones, polyetherimides, liquid-crystal polyester resins, and the like; woven fabrics obtained using composite yams comprising combinations of fibers of the above inorganic materials and fibers of the above super heat-resistant resins; and other woven fabrics including those comprising suitable combinations of the above.

In accordance with yet another embodiment of the present invention, there are provided methods for adhesively attaching a first article to a second article, said method comprising:

(a) applying die attach paste according to the invention to said first article, (b) bringing said first and second article into intimate contact to form an assembly wherein said first article and said second article are separated only by the adhesive composition applied in step (a), and thereafter, (c) subjecting said assembly to conditions suitable to cure said adhesive composition.

Articles contemplated for assembly employing invention compositions include memory devices, ASIC devices, microprocessors, flash memory devices, and the like.

Conditions suitable to cure invention die attach compositions comprise subjecting the above-described assembly to a temperature of less than about 200° C. for about 0.25 up to 2 minutes. This rapid, short duration heating can be accomplished in a variety of ways, e.g., with an in-line heated rail, a belt furnace, or the like.

In accordance with still another embodiment of the present invention, there are provided methods for adhesively attaching a microelectronic device to a substrate, said method comprising:

(a) applying die attach paste according to the invention to said substrate and/or said microelectronic device, (b) bringing said substrate and said device into intimate contact to form an assembly wherein said substrate and said device are separated only by the die attach composition applied in step (a), and thereafter, (c) subjecting said assembly to conditions suitable to cure said die attach composition.

Microelectronic devices contemplated for use with invention die attach pastes include copper lead frames (including bare copper, silver-plated copper, palladium-plated Cu, and the like), Alloy 42 lead frames, silicon dice, gallium arsenide dice, germanium dice, and the like.

In accordance with a still further embodiment of the present invention, there are provided compositions useful for protecting solder interconnections between semiconductor devices and supporting substrates, said compositions comprising:

in the range of about 20 up to about 80 wt % of a curable thermosetting acrylate-based binder system, wherein said binder system has a viscosity at room temperature of no greater than about 2,500 centipoise, and in the range of about 20 up to about 80 wt % of a filler having a maximum particle size of about 50 microns, wherein wt % is based on the total weight of the composition unless otherwise indicated, wherein said binder system comprises:

(a) cycloaliphatic bifunctional acrylate monomers having one or more of the structures VII through XII, and wherein:

A, B, R, n, n'+n", n''', m, x and x' are defined as above, (b) optionally, in the range of about 5 up to about 95 wt % of a monovinyl compound having the structure XVI as defined above;

(c) in the range of about 0.1 up to about 3 wt % of at least one free radical initiator, based on the total weight of the binder system;

(d) optionally, in the range of about 1 up to about 60 wt % of at least one polyunsaturated comonomer, based on the total weight of the binder system;

(e) optionally, a diluent, and (f) optionally, a surfactant.

Fillers contemplated for use in compositions useful for protecting solder interconnections between semiconductor devices and supporting substrates are preferably substantially spherical, or at least the majority of the filler particles are substantially spherical, so as to facilitate flow of invention composition into the gaps which form between the supporting substrate and the semiconductor device to which it is attached. Fillers suitable for use herein are further characterized as having a low coefficient of thermal expansion, as being substantially non-conductive, and as having low levels of extractable ions. In addition, fillers contemplated for use herein desirably have an emission rate of less than about 0.01 alpha particles/cm$^2$-hr.

Particle sizes of fillers employed in accordance with this embodiment of the present invention are typically 50 microns or less, preferably not greater than about 35 microns and most preferably not greater than about 25 microns. Most preferably at least about 90 weight % of the particles are no smaller than about 0.7 microns. Smaller particle sizes are necessary so that the composite polymer material will readily flow in the gap between the chip and substrate carrier. The gap is normally about 25 to about 50 microns, but in some cases is somewhat larger (e.g., about 75 to about 125 microns). Presently preferred fillers have average particle sizes in the range of about 0.5 up to about 20 micrometers, with particle sizes in the range of about 3 to about 10 microns being especially preferred, even though there may be a distribution of a minor amount of some larger particles.

In addition, according to a presently preferred aspect of this embodiment of the invention (i.e., in compositions useful for protecting solder interconnections between semiconductor devices and supporting substrates), the filler is substantially free of alpha particle emissions such as produced from the trace amounts of radioactive impurities (e.g., uranium and thorium) normally present in conventional silica or quartz fillers. The preferred fillers employed in the practice of this embodiment of the present invention have emission rates of less than 0.01 alpha particles/cm$^2$-hr and most preferably less than 0.005 alpha particles/cm$^2$-hr.

The presence of α-particle emissions (primarily caused by the presence of uranium and thorium isotopes in the fillers) can generate electron/hole pairs, which in turn would be detrimental to the device. A presently preferred filler is high purity fused or amorphous silica or synthetic glass commercial fillers which typically are rounded filler particles. A commercially available filler that can be employed is DP4910 from PQ Corporation. The preferred filler can optionally be treated with a coupling agent.

Exemplary fillers contemplated for use in accordance with this embodiment of the present invention include alumina, aluminum nitride, boron nitride, borosilicate glass, diamond dust, silica, quartz, silicon, silicon carbide, titania, zirconium tungstate, and the like, optionally treated with coupling agents and/or lubricants.

Optionally, in accordance with this aspect of the present invention, compositions contemplated for use for protecting solder interconnections can further comprise one or more of the following additional components, e.g., coupling agents, thixotropes, dyes, anti-oxidants, surfactants, inert diluents, reactive diluents, anti-bleed agents, fluxing agents, and the like.

Coupling agents (also referred to herein as adhesion promoters) contemplated for use in invention compositions useful for protecting solder interconnections between semiconductor devices and supporting substrates include silicate esters, metal acrylate salts (e.g., aluminum methacrylate), titanates (e.g., titanium methacryloxyethylacetoacetate triisopropoxide), or compounds that contain a copolymerizable group and a chelating ligand (e.g., phosphine, mercaptan, acetoacetate, and the like). When added to invention compositions, generally in the range of about 0.1 up to 5 wt % of at least one coupling agent (based on the total weight of the organic phase) will be employed, with in the range of about 0.5 up to 2 wt % preferred.

Presently preferred coupling agents contain both a co-polymerizable function (e.g., vinyl moiety, acrylate moiety, methacrylate moiety, styrene moiety, cyclopentadiene moiety, and the like), as well as a silicate ester function. The silicate ester portion of the coupling agent is capable of condensing with metal hydroxides present on the mineral surface of the substrate, while the co-polymerizable function is capable of co-polymerizing with the other reactive components of invention adhesive composition. Especially preferred coupling agents contemplated for use in the practice of the invention are oligomeric silicate coupling agents such as poly(methoxyvinylsiloxane).

Thixotropes contemplated for use in the practice of the present invention include fumed alumina, fumed silica, fumed titanium dioxide, graphite fibrils, teflon powder, organo-modified clays, thermoplastic elastomers, and the like.

Dyes contemplated for use in the practice this embodiment of the present invention include, in addition to those enumerated hereinabove, non-electrically conductive carbon black, and the like. When used, organic dyes in relatively low amounts (i.e., amounts less than about 0.2 wt %) provide contrast.

Anti-oxidants contemplated for use in this embodiment of the invention (i.e., in compositions useful for protecting solder interconnections between semiconductor devices and supporting substrates), include hindered phenols (e.g., BHT (butylated hydroxytoluene), BHA (butylated hydroxyanisole), TBHQ (tertiary-butyl hydroquinone), 2,2'-methylenebis(6-tertiarybutyl-p-cresol), and the like), hindered amines (e.g., diphenylamine, N,N'-bis(1,4-dimethylpentyl-p-phenylene diamine, N-(4-anilinophenyl) methacrylamide, 4,4'-bis(,dimethylbenzyl) diphenylamine, and the like), phosphites, and the like.

Surfactants contemplated for use in the practice of the present invention include silanes and non-ionic type surface active agents. Surfactants in amounts of about 0.5 wt % up to about 3 wt % (preferably about 1.2 wt % up to about 1.6 wt % can be used to facilitate mixing the filler with the invention resin system.

Fluxing agents contemplated for use in the practice of the present invention include propargyloxy ethers of hydroxy derivatives of aromatic carboxylic acids (e.g., the proparpyloxy ether of parahydroxy benzoic acid), and the like.

Anti-bleed agents contemplated for use in this embodiment of the invention (i.e., in compositions useful for protecting solder interconnections between semiconductor devices and supporting substrates), include cationic surfactants, tertiary amines, tertiary phosphines, amphoteric surfactants, polyfunctional compounds, and the like, as well as mixtures of any two or more thereof.

Invention compositions typically have excellent handling properties. For example, the viscosity of invention compositions at room temperature generally fall in the range of about 500 up to about 50,000 centipoise, with viscosities at room temperature in the range of about 2,000 up to about 20,000 centipoise being readily attainable.

Even where invention compositions have relatively high viscosities at room temperature, these materials have excellent handling properties at typical working temperatures (in the range of about 70° C. up to about 100° C.). Under such conditions, invention compositions typically have viscosities of no greater than about 3,000 centipoise.

Viscosity ranges for commercial epoxy-based underfills are between about 4,000–10,000 cps at 25° C. and 400–800 cps at 70° C. Two viscosity values are given per underfill because underfills are dispensed at ambient temperature and flowed at elevated temperatures (70° C.). Invention underfill materials are also capable of achieving the same performance.

The viscosity of the underfill material is dominated by the viscosity of the resin formulation, the filler morphology, filler particle size, and filler loading. Typically, very low to low viscosity resins (i.e., 50–500 cps), spherical, high purity silica filler having a diameter less than about 10 microns, and between 60–70% wt filler loadings yield underfill encapsulant of acceptable viscosity.

A particularly important consideration with respect to underfill materials is the viscosity-flow rate relationship. To a first approximation, the viscosity of the underfill can be represented as a Newtonian fluid, thus the flow rate is directly proportional to the viscosity, i.e., higher viscosity portends a slower flow rate. Since time of ingression is of critical importance to the user, the goal is typically to formulate at the lowest viscosity possible.

Common to the industry is the trend towards minimizing process times. In addition to fast flowing underfills, there is also pressure to develop low temperature, fast curing underfill materials. Traditional epoxy-based underfill materials cure slowly, necessitating an upper cure temperature limit of about 165° C. over a 1–2 hour period. In the last few years, epoxy snap cure materials have emerged, curing at temperatures as low as 130° C. for less than about 15 minutes are typical.

The vinyl monomer-based underfill materials of the present invention achieve both low temperature and fast cure. The free radical, addition polymerization cure mechanism yields acrylic resin systems which are stable at the flow temperature (70° C.) but cure rapidly above about 100° C. Typical to an acrylic resin system is a cure onset range between about 100–130° C. and a cure peak maximum at between about 120–150° C. The final cure properties are developed within 15 minutes of cure.

High purity, spherical, silica filler is the industry standard. Most epoxy encapsulants use a size fraction either below 5 micron or between 5 and 10 microns. These ranges allow the underfill material to ingress as rapidly as possible while minimizing separation and settling from the resin upon ingression.

The only function of filler in underfill applications is to lower the coefficient of thermal expansion (CTE). By blending silica filler (having a CTE of about 2.5 ppm) and the resin (~80–200 ppm), the CTE can be lowered close to the CTE of the solder bumps (18 ppm). Thus, CTE controls the level of filler used within a system.

Many of the standards used over the last few years are changing due to the changing dimensions of the flip chip, and CTE is no exception. The trend toward the lowest CTE achievable seems to giving way to a much broader range of between about 25–50 ppm. Thus most of the underfill materials according to the invention possess CTE values between about 28–38 ppm.

The glass transition is considered to be the upper working temperature of the underfill. Since it is the function of the underfill to support the bumps by immersing them in a rigid environment capable of dissipating the stress caused by thermal cycling, the temperature at which the encapsulant transitions from its glass phase to rubbery phase is critical. Typically, $T_g$s for epoxy underfills are between about 130 and 160° C., but there are many epoxy materials with $T_g$s as low as 110° C. The vinyl monomer-based encapsulants described herein are typically high $T_g$ materials, typically well above 160° C., and more in the range of 200° C. or greater.

As noted above, underfill materials work by supporting the bumps (the electrical interconnects between the die and the substrate) in an high modulus encapsulant, and the "stiffness" (elastic moduli) of the encapsulant has been strongly correlated to the electrical reliability enhancement induced by encapsulation. For example, "hard" (8–10 GPa) encapsulants yield higher reliability (able to survive more thermal cycles, i.e., −55 to +150° C., without loss of continuity) than "soft" (4–6 GPa) encapsulants. Most of the vinyl monomer-based encapsulants described herein are between 4–8 GPa. Although this range is midway between the two ranges listed above, the elastic modulus ranges for successful encapsulation is also in redefinement in the industry, especially with the shrinking of the bump height (i.e., 1 mil).

In summary, the properties of invention underfill materials can be compared to typical properties of prior art epoxy-based materials as follows:

| Parameter | Commercial (epoxy) | Invention |
| --- | --- | --- |
| Viscosity | | |
| at 25° C. | 4,000–10,000 cps | 4,000–10,000 cps |
| at 70° C. | 400–800 cps | 400–800 cps |

-continued

| Parameter | Commercial (epoxy) | Invention |
|---|---|---|
| Cure Speed | 15 to 60 minutes | <15 minutes |
| Cure Temperature | 150–165° C. | 130–165° C. |
| CTE | 22–28 ppm | 28–38 ppm |
| $T_g$ | 110–160° C. | >160° C. |
| Elastic Modulus | 6–10 GPa | 4–8 GPa |

In accordance with yet another embodiment of the present invention, there are provided methods for protecting solder interconnections between semiconductor devices and supporting substrates therefor, said methods comprising:

attaching said device to said substrate by a plurality of solder connections that extend from the supporting substrate to electrodes on said semiconductor device, thereby forming a gap between said supporting substrate and said semiconductor device, filling said gap with a composition according to the invention, and subjecting said composition to curing conditions.

Substrates contemplated for use herein can be based on either organic material, inorganic material, or combinations thereof. For example, organic substrates contemplated for use herein include thermoplastic and thermosetting resins. Typical thermosetting resinous materials include epoxy, phenolic-based materials, polyimides and polyamides. Such materials are usually molded of the resinous material along with a reinforcing agent such as a glass-filled epoxy or phenolic-based material. Examples of some phenolic-type materials include copolymers of phenol, resorcinol, and cresol. Examples of some suitable thermoplastic polymeric materials include fluorinated polymeric materials, polyolefins such as polypropylene, polysulfones, polycarbonates, nitrile rubbers and ABS polymers.

Selection of a particular organic resin will depend in part on the processing temperatures that the substrate will be subjected to during the soldering. For example, fluorinated polymeric materials contemplated for use herein are well-known and include such commercially available polyfluoroalkylene materials as polytetrafluoroethylene, copolymers of tetrafluoroethylene and hexafluoropropylene, copolymers of tetrafluoroethylene and perfluoro-2,2-dimethyl-1,3 dioxide, polytrifluorochloroethylene, copolymers of tetrafluoroethylene with, for example, olefins such as ethylene; copolymers of trifluoromonochloroethylene with for example olefins such as ethylene, polymers of perfluoroalkyl vinyl ether.

Some commercially available fluorinated polymeric materials which are suitable for use in the practice of the present invention include those available under the trade designation TEFLON PTFE (polymers of tetrafluoroethylene), TEFLON FEP (perfluorinated ethylene-propylene copolymers); TEFLON PFA (copolymer of tetrafluoroethylene and perfluoroalkoxy); TEFZEL (copolymer of tetrafluoroethylene and ethylene); HALAR (copolymer of chlorotrifluoroethylene and ethylene); KEL-F (polymer of chlorotrifluoroethylene); HBF-430 (polymer of chlorotrifluoroethylene) and TEFLON AF (copolymer of tetrafluoroethylene and at least 65 mole % of perfluoro-2, 2-dimethyl-1,3 dioxide). The preferred fluorinated polymeric material is polytetrafluoroethylene (e.g., TEFLON). Commercially available fluorocarbon polymers reinforced with fiber glass are available from Rogers Corporation under the trade designation R02800 and R02500.

The polyimides that can be used as substrates in accordance with this aspect of the present invention include unmodified polyimides, as well as modified polyimides such as polyester imides, polyamide-imide-esters, polyamide-imides, polysiloxane-imides, as well as other mixed polyimides. Such are well-known in the prior art and need not be described in any great detail herein.

Typical epoxy resins employed as substrates for this aspect of the present invention include the bisphenol A type resins obtained from bisphenol A and epichlorohydrin, resinous materials obtained by the epoxidation of novolak resins (produced from a phenolic material such as phenol and an aldehyde such as formaldehyde) with epichlorohydrin, polyfunctional epoxy resins such as tetraglycidyldiaminodiphenyl methane and alicyclic epoxy resins such as bis(3,4-epoxy-6-methylcyclohexylmethyl) adipate. The presently most preferred epoxy employed in the practice of the present invention is the bisphenol A type.

The epoxy resinous compositions also can contain accelerating agents and curing agents as are well-known in the art. Examples of suitable curing agents include polyamines, primary, secondary, and tertiary amines, imidazoles, polyamides, polysulfides, urea-phenol-formaldehyde, and acids or anhydrides thereof. In addition, suitable curing agents include Lewis acid catalysts such as $BF_3$ and complexes thereof, onium salts, sulfonium salts, and the like.

Many of the organic substrates employed in this aspect of the present invention contain the resin and a reinforcing fiber such as fiberglass, polyamide fiber mats (e.g., Kevlar), graphite fiber mats, Teflon fiber mats, and the like. Such compositions containing fibers are usually prepared by impregnating the fibers with, for instance, a composition of a suitable polymer. The amount of the polymer composition is usually about 30% to about 70% by weight (with about 50% to about 65% by weight preferred) of the total solids content of the polymer composition of the fiber support.

In the case of epoxy compositions, for example, such can be prepared by combining with the reinforcing fibers, and then curing to the B-stage and cutting to the desired shape, such as a sheet. When sheets are employed, the thickness is usually about 1.5 mils to about 8 mils. Curing to the B-stage is generally achieved by using temperatures of about 80° C. to about 110° C. for about 3 minutes to about 10 minutes.

If desired, the substrate can then be laminated onto other substrates as well as being interposed between the above electrically conductive patterns present in the support layers. The laminating can be carried out by pressing together the desired structure in a preheated laminating press at a predetermined pressure and temperature as, for example, about 200 psi to about 300 psi at about 180° C. The time of the pressing operation is variable depending upon the particular materials employed and the pressure applied. About 1 hour is adequate for the above conditions.

The organic substrates include the desired electrically conductive circuitry on the top and/or bottom surfaces of the substrate and/or on interior planes of the substrate as well known.

Next, in order to connect the electrically conductive patterns on opposing surfaces of the dielectric material, through-holes in the structure can be made. The through-holes can be obtained by drilling or punching operations including mechanical drilling and laser drilling and subsequently plated.

The organic substrates are generally about 3 to about 300 mils thick and more usually about 40 to about 100 mils thick.

Inorganic substrates contemplated for use herein include silicon supports, ceramic supports (e.g., silicon carbide supports, aluminum nitride supports, alumina supports, berrylia supports, and the like), sapphire supports, porcelain coated on steel, and the like.

Dispense and flow conditions employed for applying invention compositions are preferably selected such that the composition forms fillets on all four side walls of the chip. Thus, invention compositions can be applied by dispensing through nozzles under pressure of about 15 to about 90 psi and temperatures of about 25° C. to about 90° C. The compositions preferably completely cover the solder bump interconnections.

If desired, the flow of the compositions under the chip can be accelerated by heating for about 2 to about 20 minutes, typically about 15 minutes at about 40° C. to about 90° C.

Also, if desired, the compositions can be pregelled by heating for about 6 to about 60 minutes typically about to about 15 minutes at about 110° C. to about 130° C. and preferably about 6 to about 10 minutes at about 115° C. to about 120° C.

Curing conditions contemplated for use in the practice of the present invention comprise subjecting the composition to a temperature of up to about 170° C. for up to about 2 hours. Preferably, curing will be carried out at a temperature of up to about 150° C. for up to about 1 hour, with curing at temperatures below about 140° C. for up to about 0.5 hour being presently preferred.

In accordance with still another embodiment of the present invention, there are provided articles comprising a circuit board having a solder mask deposited thereon, wherein said solder mask is prepared from compositions according to the invention. When used for this purpose, it is preferred that invention compositions contain no filler, which is usually avoided in such applications.

Conditions suitable to cure invention compositions when used for the preparation of solder mask include thermal curing (as detailed hereinabove) as well as light initiated curing (employing, for example, visible light, ultraviolet, infrared irradiation, and the like).

In accordance with a still further embodiment of the present invention, there are provided articles comprising an electronic component encased within an aliquot of composition according to the invention. When used for this purpose, filler is commonly included is such compositions. Presently preferred fillers employed for such purpose include silica, alumina, and the like.

It is especially desirable that the material applied to encase an electronic component therein be handled and dispensed in such a manner that the introduction of voids in the encapsulation material is avoided.

In a further embodiment of the present invention, there are provided methods of for the preparation of an acrylate derivative of an oligomer of cyclopentadiene, said method comprising:

(a) combining said oligomer with formate in the presence of a free radical initiator to obtain a formate derivative of said oligomer, (b) subjecting said formate derivative to either acid or base hydrolysis to obtain an alcohol derivative of said oligomer, and (c) combining said alcohol derivative with (meth) acrylate to obtain one or more acrylate derivatives of said oligomer of cyclopentadiene.

As will be understood by those of skill in the art, the parameters for the above-described reactions may vary depending on the nature and purity of starting materials, and the like. Accordingly, in one embodiment of the present invention, the formate derivative of the oligomer of cyclopentadiene is prepared by combining approximately equal volumes of oligomerized cyclopentadiene and formic acid and heating at a temperature in the range of about 45° C. up to about 65° C. until the bulk of oligomerized cyclopentadiene is dissolved. At this point, the reaction temperature is raised to a temperature in the range of about 101° C. up to 110° C. and reflux is continued for about 3–5 hours. Excess formic acid is removed by suitable means (e.g., by distillation or the like), resulting in a crude formate derivative of oligomerized cyclopentadiene. This crude formate may be further purified by distillation or like methods.

The formate derivative of oligomerized cyclopentadiene is then subject to acid or base hydrolysis by methods known to those of skill in the art. In one aspect of invention methods, the formate derivative of oligomerized cyclopentadiene is combined with an approximately equal volume of aqueous sodium hydroxide (approximately 25 wt %) and the combination is heated to a temperature in the range of 80–100° C. for about 5 to 10 hours. After being allowed to cool, most of the aqueous portion of the combination is removed (e.g., by use of a separatory funnel or the like), leaving behind the alcohol derivative of oligomerized cyclopentadiene. For optimum results, the pH of the alcohol is adjusted to neutral by, for example, repeatedly washing with water. In a presently preferred aspect, most of the water is subsequently removed (e.g., by distillation in the presence of an equal volume of cyclohexane, or like techniques).

Acrylation of the alcohol derivative of oligomerized cyclopentadiene may also be accomplished by any method known to those of skill in the art. In one aspect of the present invention, the alcohol is combined with one-half volume of an acrylate such as methyl acrylate and an inhibitor (e.g., a mixture of 500 ppm TEMPO (2,2,6,6-tetramethyl-1-piperidinyloxy) and 250 ppm phenothiazine, or the like). The combination is heated to reflux and the distillate boiling below about 70° C. is removed. In a presently preferred embodiment, a small volume of a Lewis Acid such as titanium tetraisopropoxide is then added. In this latter embodiment, reflux is again continued for in the range of about 4 up to about 6 hrs, during which time the distillate fraction boiling at about 53–55° C. is removed. Substantially complete conversion of the alcohol to acrylate is indicated by a distillate temperature reaching and maintaining a temperature in the range of about 69–70° C.

The invention will now be described in greater detail by reference to the following non-limiting examples.

EXAMPLE 1

Preparation of Acrylated Oligomerized Cyclopentadiene

Oligomerization of Dicyclopentadiene

Dicyclopentadiene (DCPD) (>95%, BHT stabilized) was added to a reactor flask equipped with a heating mantle, thermometer, overhead stirrer, condenser, and nitrogen supply line. The contents were heated to reflux and reflux maintained over the next 18 hours. Due to oligomerization of the DCPD, the temperature was gradually increased over the 18 hours from 155° C. to 165° C. to maintain reflux. Unreacted DCPD was distilled from the flask at less than 1 mmHg between 45° C. and 100° C. Typical yields of oligomerized DCPD ranged between 50% and 60% of initial reactant weight. A thick, white slurry of oligomerized DCPD remained.

Esterification of Oligomerized DCPD with Formic Acid

Oligomerized DCPD and an equal volume of formic acid (>95%) were added to a reactor flask equipped with a heating mantle, thermometer, overhead stirrer, condenser, and nitrogen supply line. The contents were heated to about 50–60° C., during which the bulk of the oligomerized DCPD dissolved and reacted. After the initial exotherm had subsided, the contents were heated to 105–110° C. for 4 hours.

After cooling, excess formic acid was distilled away at low vacuum between 60° C. and 110° C. The crude formate was purified by short-path distillation at less than 0.1 mmHg at 180° C., resulting in a clear, low viscosity oily liquid (90–95% yield) of crude formate.

Formate Hydrolysis

Formate prepared according to the preceding paragraph and an equal volume of aqueous sodium hydroxide (25% by wt.) were added to a reactor flask equipped with a heating mantle, thermometer, overhead stirrer, condenser, and nitrogen supply line. Under vigorous stirring, the contents was heated to 85–95° C. for 6–8 hours. After cooling, the bulk of the aqueous solution was removed by separation, leaving a viscous, lightly colored liquid (alcohol). The alcohol was repeatedly washed (i.e. 3–5 times) with about 0.5 to 1 volume of water under slow agitation until the pH of the wash was neutral. Following, about an equal volume of cyclohexane was added, and the flask was equipped with a Dean-Stark trap. The contents of the flask were then refluxed until no more water distilled from the flask to the Dean-Stark trap. The final solution was a light brown, low viscosity liquid comprising alcohol and cyclohexane.

Acrylation

The alcohol mixture (i.e., alcohol and cyclohexane prepared according to the previous paragraph) and an equal volume of cyclohexane were added to a reactor flask equipped with a heating mantle, thermometer, overhead stirrer, and an efficient fractional distillation column fitted with a splitter and condenser. Next, a one-half volume (relative to alcohol mixture) of freshly distilled methyl acrylate containing 500 ppm TEMPO (2,2,6,6-tetramethyl-1-piperidinyloxy) and 250 ppm phenothiazine was added to the flask. The contents were heated to reflux and dehydrated by removing the distillate boiling below 69–70° C. (via the splitter above the column). Next, a small volume of titanium tetraisopropoxide was added to the flask and reflux was continued. Over the next 4–6 hours, distillate boiling at 53–55° C. was removed via the splitter. Full conversion of the alcohol to the acrylate was signified when the distillate temperature steadily increased to and maintained at 69–70° C.

Upon cooling, the bulk of the solvent (cyclohexane and excess methyl acrylate) was removed using a rotary evaporator under reduced pressure and low temperature (40–50° C.). The residue was then diluted with 3–4 volumes of octane followed by the addition of a small volume of methane sulfonic acid was added to remove the inhibitors. The solids were then removed via filtration, and the mixture transferred to a separatory funnel and washed 3–5 times with about 0.5 to 1 volume of water until a neutral pH was reached. The mixture was dried over anhydrous magnesium sulfate and decolorized over a small volume of activated charcoal. The solids were removed by passing the solution over a bed of silica gel followed by removal of the solvent via a rotary evaporator at reduced pressure and low temperature. Trace levels of solvent were removed by sparging the residue with air overnight (12–16 hours) followed by degassing at high vacuum. The final acrylate was a light yellow, medium viscosity liquid.

EXAMPLE 2

In order to test the adhesive properties of an invention formulation, a die attach paste was made using the acrylate monomer described in Example 1. An organic adhesive base was made by mixing 53.6 parts of the acrylate from Example 1, 15.2 parts liquid bismaleimide resin (1,20-bismaleimido-10,11-dioctyl-eicosane, which likely exists in admixture with other isomeric species produced by thermal reaction of oleic acids, or like reactions), 15.2 parts R130 polybutadiene (Ricon Resins, Bolder, Colo.), 5.4 parts Ricon R130-20MA, 2.0 parts dicumyl peroxide catalyst, 7.0 parts QM57 [2-(dicylcopentenyloxy)ethyl acrylate], 1.0 part OSi (Endicott, N.Y.) A-186 [beta-(3,4-poxycyclohexyl) ethyltrimethoxysilane], and 0.7 parts palladium methacrylate. Twenty-one parts of this organic adhesive base were mixed with 79.0 parts of silver flake to make the final die attach paste. This paste was designated "1211-79A".

Using the paste, eighteen parts were assembled on silver plated copper lead frames and fourteen mil thick 300×300 mil bare silicon die. The parts were cured on a hotplate at 200° C. for one minute. A set of eighteen control parts was also assembled using Ablestick 8360 (a widely used epoxy-based die attach adhesive). The 8360 parts were oven cured at 175° C. for one hour (consistent with the manufacturer's guidelines). Tests were performed on both groups of parts including radius of curvature (ROC) before and after a 184 hour exposure to 85% humidity at 85° C., and die shear adhesion (conducted at room temperature and 245° C.). The results of these tests are summarized in Table 1.

TABLE 1

Comparison of an Invention Acrylate-Based Adhesive to Ablestick 8360

| Material | Ablestick 8360 | Invention Formulation |
| --- | --- | --- |
| Initial ROC (meters) | 0.44 ± 0.03 | 0.41 ± 0.03 |
| Post 85/85 ROC (meters) | 0.59 ± 0.06 | 0.44 ± 0.02 |
| RT Die Shear (Kg force) | 47.6 ± 9.6 | 69.9 ± 11.4 |
| 245° C. Die Shear (Kg force) | 5.4 ± 1.7 | 10.2 ± 2.2 |

The Ablestick 8360 adhesive had a thirty-four percent increase in radius of curvature after exposure to 85% humidity at 85° C. (85/85 exposure), while the ROC for the invention acrylate paste increased by only seven percent under the same hot/moist conditions. This difference in ROC is believed to be directly related to the relative hydrophobicity of these two formulations. The 8360 epoxy adhesive has a higher affinity for moisture and is therefore plasticized by the 85/85 exposure. The invention formulation is much more hydrophobic and therefore is much less affected by the 85/85 test conditions. The invention formulation also has superior adhesion performance at both room temperature and 245° C. die shear conditions compared to the 8360 adhesive. It is also noteworthy that all of the properties of the invention formulation were superior to those of the 8360 adhesive despite the much shorter cure schedule (i.e. one minute versus one hour).

EXAMPLE 3

Additional testing was done using the invention formulation described in Example 2 versus Ablestick 8360. Thirty-eight parts were assembled for each of these die attach compositions using fourteen mil thick 150×150 mil silicon die on bare copper lead frames. The cure conditions were identical to those used in Example 2. Ten parts from each group were tested for initial die shear adhesion. Another ten parts from each group were subjected to Jedec level 1 conditioning (85% humidity, 85° C. for 168 hours followed by three immersions in a 235° C. reflow). Finally, eighteen parts from each group were encapsulated with Nitto 7450 molding compound and then subjected to the Jedec level 1 conditioning as molded packages. The die shear adhesion results for the initial die attached parts are shown in Table 2. The die shear adhesion results for the bare parts following Jedec level 1 conditioning are shown in Table 3.

TABLE 2

| Initial Die Shear Adhesion | | |
|---|---|---|
| Die Shear Condition | 1211-79A | Ablestick 8360 |
| Room Temperature | 33.9 ± 2.3 | 25.3 ± 3.9 |
| 245° C. | 6.2 ± 1.4 | 1.9 ± 0.5 |

TABLE 3

| Die Shear Strength after Jedec Level 1 Exposure | | |
|---|---|---|
| Die Shear Condition | Invention Formulation | Ablestick 8360 |
| Room Temperature | 41.7 ± 7.9 | 27.4 ± 11 |
| 245° C. | 9.1 ± 1.1 | 1.4 ± 0.2 |
| 245° C., % Change | +12% | −26% |

The molded parts that had been subjected to Jedec level 1 conditioning were evaluated using SONOSCAN™ acoustic microscopy. This method is a common non-destructive test that is used to search for delamination between various interfaces within molded parts. The molded parts following Jedec level 1 conditioning showed a dramatic difference between the invention formulation and the Ablestick 8360. All (i.e. eighteen out of eighteen parts) of the 8360 adhered parts showed delamination by acoustic microscopy, while none (i.e., zero out of eighteen) of the invention formulation adhhered parts showed any delamination. These results are consistent with the superior hydrophobicity of the invention formulation demonstrated in Example 2.

Delamination in molded packages is a serious problem during the manufacture of microelectronic components. Moisture absorbed into either the mold compound or die attach material can lead to catastrophic failure during subsequent solder reflow assembly operations. This failure is widely known in the industry as "popcorning". Popcorning is unacceptable in the assembly of printed wiring boards since the "popcorned" part will result in immediate, or at least accelerated, electronic failure of the entire circuit board. Jedec level 1 is considered to be the most aggressive test used to predict the likelihood of such failures. It is highly advantageous to have a die attach material that can pass Jedec level 1 tests since this performance ensures that the assembly of boards made with this material will be defect-free under normal assembly conditions. It also eliminates a major burden on the manufacturer since there would no longer be any need to rigorously control the environmental moisture that the molded parts are subject to prior to solder reflow.

While the invention has been described in detail with reference to certain preferred embodiments thereof, it will be understood that modifications and variations are within the spirit and scope of that which is described and claimed.

That which is claimed is:

1. An acrylate derivative of oligomers of optionally substituted cyclopentadiene.

2. An acrylate according to claim 1, wherein said oligomers comprise one or more bicyloheptane moieties.

3. An acrylate according to claim 2, wherein each of said bicycloheptane moieties is independently substituted with 0, 1 or 2 substituents independently selected from the group consisting of lower alkyls or halogens.

4. An acrylate according to claim 1, wherein said oligomers comprise one or more of the following structures:

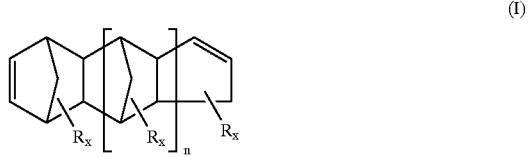

(I)

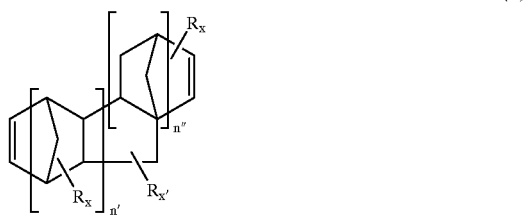

(II)

wherein:

each R is independently a lower alkyl or a halogen, n is 1, 2 or 3 the sum of n'+n" is 1, 2 or 3 each x is independently 0, 1 or 2, and x' is 0, 1, 2.

5. An acrylate derivative of optionally substituted bicycloheptenyl-containing optionally substituted polycyclic moieties.

6. An acrylate derivative according to claim 5, wherein said optionally substituted bicycloheptenyl-containing optionally substituted polycyclic moieties are selected from one or more of the following structures:

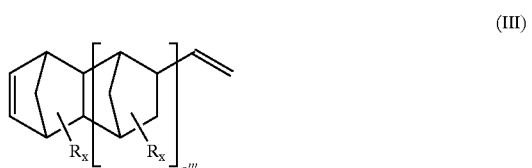

(III)

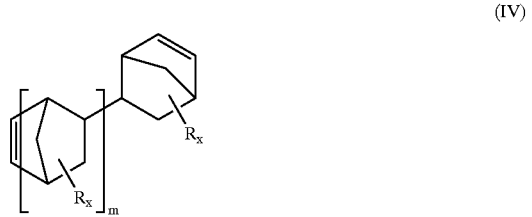

(IV)

wherein:

each R is independently a lower alkyl or a halogen, n''' is 1, 2, 3, 4, or 5, m is 1, 2, 3, 4,or 5, each x is independently 0, 1 or 2, and x' is 0, 1, 2.

7. A bifunctional acrylate monomer having one or more of the following structures:

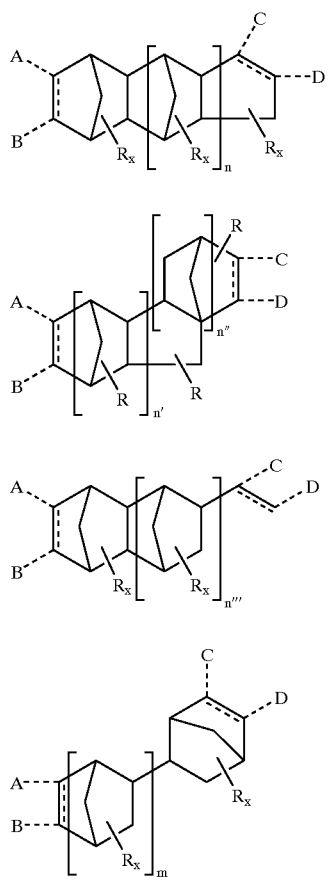

(V)

(VI)

(VII)

(VIII)

wherein:

at least one of A and B, and/or one of C and D is a (meth)acrylate moiety, wherein any of A, B, C, and D that are not (meth)acrylate are H or a functional group, each R is independently a lower alkyl or a halogen, n is 1, 2 or 3, the sum of n'+n" is 1, 2 or 3, n''' is 1, 2, 3, 4, or 5, m is 1, 2, 3, 4, or 5, each x is independently 0, 1 or 2, and x' is 0, 1, 2.

8. A bifunctional monomer according to the following structure:

X—Y—Z wherein:

Y is an optional bridging group,

X is an acrylate derivative of an oligomer of optionally substituted cyclopentadiene, a radical having one of the following structures:

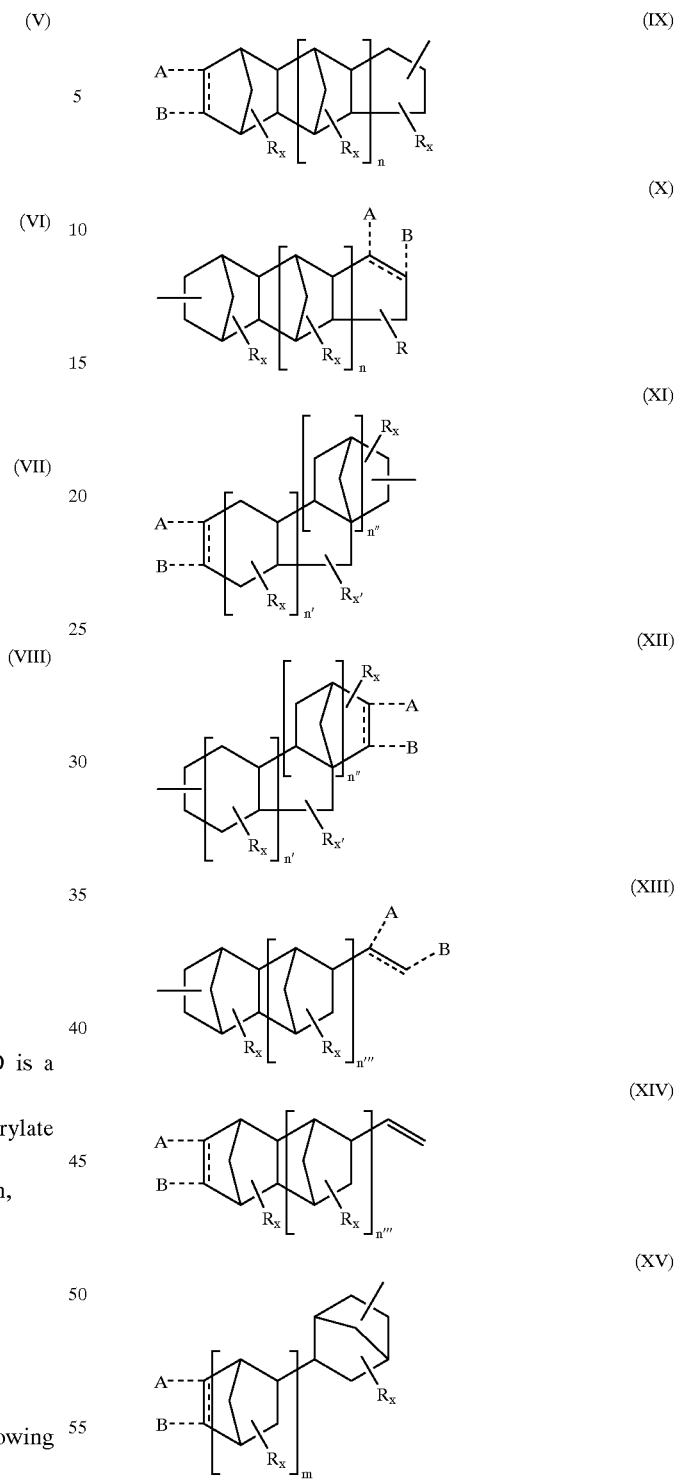

(IX)

(X)

(XI)

(XII)

(XIII)

(XIV)

(XV)

wherein:

A or B is a (meth)acrylate moiety, wherein the non-(meth)acrylate member of the A/B pair is H, each R is independently a lower alkyl or a halogen, n is 1, 2 or 3 the sum of n'+n" is 1, 2 or 3, n''' is 1, 2, 3, 4, or 5, m is 1, 2, 3, 4, or 5, each x is independently 0, 1 or 2, and x' is 0, 1, 2, and Z is a trimer, tetramer or pentamer of optionally substituted cyclopentadiene bearing at least one functional group, a radical having one of said structures (IX), (X), (XI), (XII), (XIII), (XIV) or (XV), an epoxy, or a cycloaliphatic moiety bearing at least one functional group.

9. A bifunctional monomer according to claim 8, wherein Z is an oligomer of optionally substituted cyclopentadiene bearing at least one functional group, or a radical having one of said structures (IX), (X), (XI), (XII), (XIII), (XIV) or (XV).

10. A bifunctional monomer according to claim 9, wherein X is an (oxy) alkylene, an (oxy) arylene or a siloxane.

11. A bifunctional monomer according to claim 10, said siloxanes having the structure:

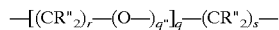

wherein:

each R'' is independently hydrogen, a lower alkyl or aryl, each R''' is independently selected from hydrogen, oxygen, lower (oxy) alkyl or (oxy) aryl, m' falls in the range of 0 up to about 10, m'' falls in the range of 0 up to about 10, and q' falls in the range of 1 up to 50.

12. A bifunctional monomer according to claim 10, wherein said (oxy) alkylenes have the structure:

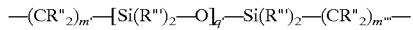

wherein:

each R'' is independently selected from hydrogen, lower alkyl or aryl, m' falls in the range of 1 up to about 10, m''' falls in the range of 1 up to about 10, q'' is 0 or 1 and q falls in the range of 1 up to 50.

13. A bifunctional monomer according to claim 8, wherein said substituents are independently lower alkyl or halogen.

14. A bifunctional monomer according to claim 8, wherein said functional groups are maleimido, norbornenyl, cyanate ester, anhydride, carboxylic acid, epoxide, amide, sulfide, or polyhydroxy hydrocarbyl.

* * * * *

UNITED STATES PATENT AND TRADEMARK OFFICE
CERTIFICATE OF CORRECTION

PATENT NO.   : 6,211,320 B1
DATED        : April 3, 2001
INVENTOR(S)  : Dershem et al.

It is certified that error appears in the above-identified patent and that said Letters Patent is hereby corrected as shown below:

Column 4, line 45, and at Column 30, line 15,

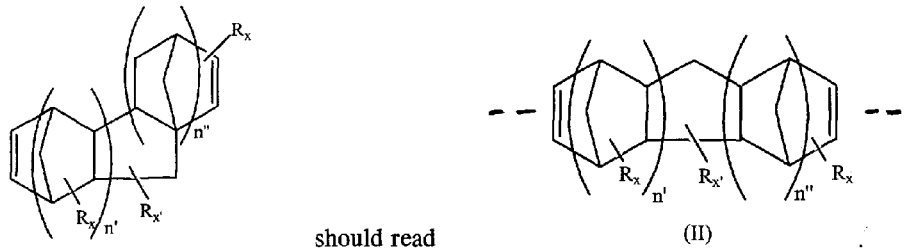

Column 5, line 40, and at Column 31, line 15,

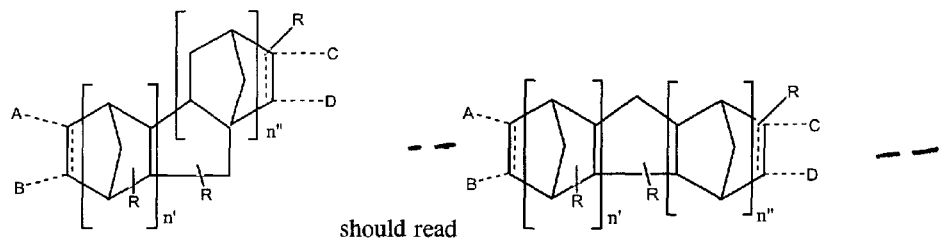

Column 6, line 60, and at Column 32, line 20,

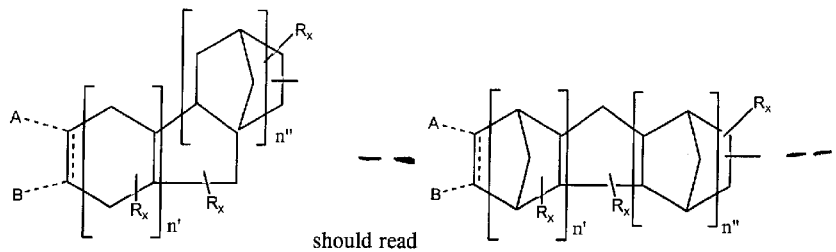

UNITED STATES PATENT AND TRADEMARK OFFICE
CERTIFICATE OF CORRECTION

PATENT NO. : 6,211,320 B1
DATED : April 3, 2001
INVENTOR(S) : Dershem et al.

It is certified that error appears in the above-identified patent and that said Letters Patent is hereby corrected as shown below:

Column 7, line 5, and at Column 32, line 30,

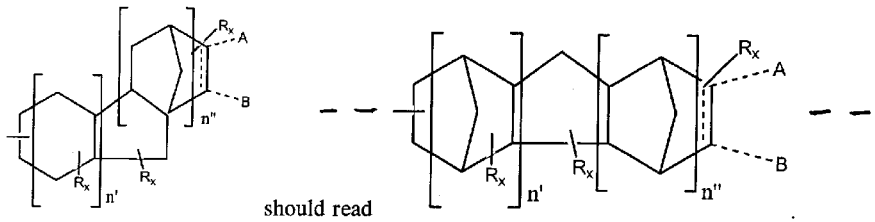

Column 13,
Line 60,

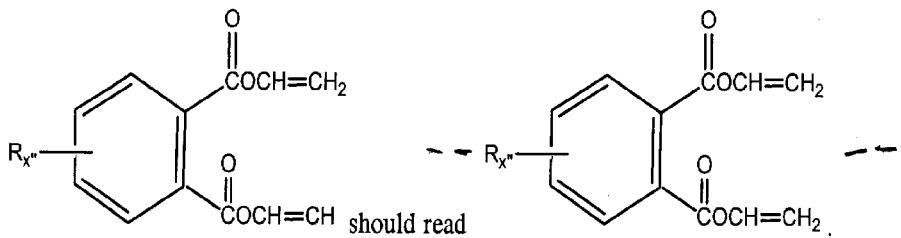

Column 14,
Line 5,

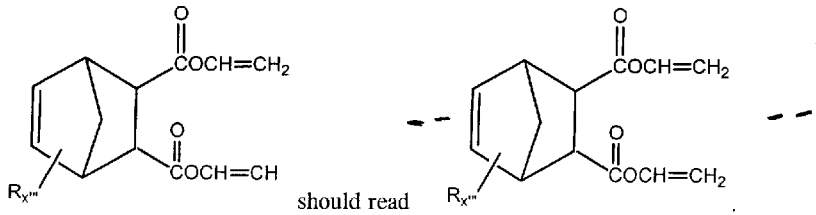

UNITED STATES PATENT AND TRADEMARK OFFICE
CERTIFICATE OF CORRECTION

PATENT NO.   : 6,211,320 B1
DATED        : April 3, 2001
INVENTOR(S)  : Dershem et al.

It is certified that error appears in the above-identified patent and that said Letters Patent is hereby corrected as shown below:

Column 14,
Line 35,

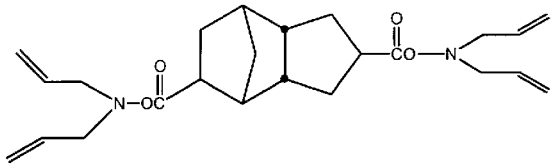

should read

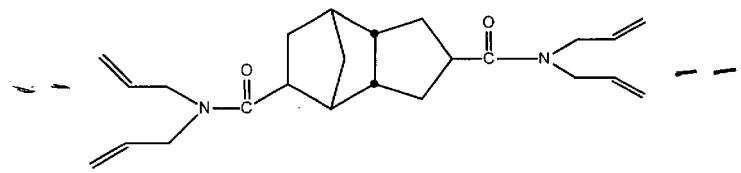

Signed and Sealed this

Twenty-fifth Day of March, 2003

JAMES E. ROGAN
*Director of the United States Patent and Trademark Office*